(12) United States Patent
Yock

(10) Patent No.: US 6,575,993 B1
(45) Date of Patent: *Jun. 10, 2003

(54) ANGIOPLASTY APPARATUS FACILITATING RAPID EXCHANGES

(76) Inventor: Paul G. Yock, 1216 San Mateo Dr., Menlo Park, CA (US) 94025

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/485,397

(22) Filed: Jun. 7, 1995

Related U.S. Application Data

(63) Continuation of application No. 08/208,972, filed on Mar. 9, 1994, now Pat. No. 5,451,233, which is a division of application No. 08/010,458, filed on Jan. 27, 1993, now Pat. No. 5,300,085, which is a continuation of application No. 07/937,977, filed on Nov. 2, 1992, now Pat. No. 5,350,395, which is a continuation of application No. 07/774,479, filed on Oct. 10, 1991, now abandoned, which is a continuation of application No. 07/548,200, filed on Jul. 5, 1990, now Pat. No. 5,061,273, which is a continuation of application No. 07/361,676, filed on Jun. 1, 1989, now abandoned, which is a continuation of application No. 07/117,357, filed on Oct. 27, 1987, now abandoned, which is a continuation of application No. 06/852,197, filed on Apr. 15, 1986, now abandoned.

(51) Int. Cl.$^7$ ............................................. A61M 25/10
(52) U.S. Cl. ................................. 606/194; 604/103.04
(58) Field of Search ......................... 606/194, 192, 606/193, 191; 604/96, 103.04

(56) References Cited

U.S. PATENT DOCUMENTS

| | | | |
|---|---|---|---|
| 1,596,284 A | 8/1926 | Malmgren | |
| 2,043,083 A | 6/1936 | Wappler | 128/303.11 |
| 2,687,131 A | 8/1954 | Raiche | 128/349 |
| 2,883,986 A | 4/1959 | de Luca et al. | 128/351 |
| 2,936,760 A | 5/1960 | Gants | 128/349 |
| 3,435,826 A | 4/1969 | Fogarty | |
| 3,467,101 A | 9/1969 | Fogarty et al. | |
| 3,731,692 A | 5/1973 | Goodyear | 128/351 |
| 3,769,981 A | 11/1973 | McWhorter | 128/348 |
| 3,882,852 A | 5/1975 | Sinnreich | 128/4 |

(List continued on next page.)

FOREIGN PATENT DOCUMENTS

| | | |
|---|---|---|
| FR | 591963 | 4/1925 |
| FR | 2254351 | 11/1975 |
| RU | 627828 | 10/1978 |

OTHER PUBLICATIONS

Nordenstrom ACTA Radiology, vol. 57, Nov. 1962, pp. 411–416.
Nordenstrom, Radiology, vol. 85, pp. 256–259 (1965).
S. Thomson, "Disease of the Nose and Throat," pp. 776, 794–797, 6th Ed., 1955.
Tassilo Bonzel, "A New PTCA System with Improved Steerability, Contrast Medium Application and Exchangeable Intracoronary Catheters," *PTCA Proc. Abstract*, Course 3, Center for Cardiology, University Hospital, Geneva, Switzerland, Mar. 24–26, 1986.

(List continued on next page.)

*Primary Examiner*—Michael H. Thaler
(74) *Attorney, Agent, or Firm*—Fulwider Patton Lee & Utecht, LLP

(57) ABSTRACT

Apparatus for introduction into the vessel of a patient comprising a guiding catheter adapted to be inserted into the vessel of the patient and a device adapted to be inserted into the guiding catheter. The device includes a flexible elongate member and. a sleeve carried by the flexible elongate member near the distal extremity thereof and extending from a region near the distal extremity to a region spaced from the distal extremity of the flexible elongate element. The device also includes a guide wire adapted to extend through the sleeve so that the guide wire extends rearwardly of the sleeve extending alongside of and exteriorly of the flexible elongate element into a region near the proximal extremity of the flexible elongate element.

10 Claims, 3 Drawing Sheets

U.S. PATENT DOCUMENTS

| | | | |
|---|---|---|---|
| 4,195,637 A | 4/1980 | Gruntzig et al. | |
| 4,198,981 A | 4/1980 | Sinnreich | 128/344 |
| 4,289,128 A | 9/1981 | Rusch | 128/207 |
| 4,299,226 A | 11/1981 | Banka | 128/344 |
| 4,307,722 A | 12/1981 | Evans | |
| 4,311,133 A | 1/1982 | Robinson | |
| 4,323,071 A | 4/1982 | Simpson-Robert | |
| 4,362,150 A | 12/1982 | Lombardi et al. | |
| 4,367,747 A | 1/1983 | Witzel | 128/344 |
| 4,385,631 A | 5/1983 | Uthmann | 604/281 |
| 4,423,725 A | 1/1984 | Baran et al. | |
| 4,444,188 A | 4/1984 | Bazell et al. | |
| 4,468,224 A | 8/1984 | Enzmann et al. | 604/247 |
| 4,545,390 A | 10/1985 | Leary | |
| 4,554,929 A | 11/1985 | Samson-Solar | |
| 4,569,347 A | 2/1986 | Frisbie | |
| 4,573,470 A * | 3/1986 | Samson et al. | 606/194 |
| 4,581,017 A | 4/1986 | Sahota | |
| 4,610,662 A | 9/1986 | Weikl et al. | 604/53 |
| 4,616,653 A | 10/1986 | Samson et al. | |
| 4,619,263 A | 10/1986 | Frisbie et al. | |
| 4,652,258 A | 3/1987 | Drach | 604/53 |
| 4,662,368 A | 5/1987 | Hussein et al. | 606/7 X |
| 4,664,113 A * | 5/1987 | Frisbie et al. | 606/194 |
| 4,665,925 A * | 5/1987 | Millar | 128/663 |
| 4,762,128 A | 8/1988 | Rosenbluth | |
| 4,967,745 A | 11/1990 | Hayes et al. | |

OTHER PUBLICATIONS

Thomson, Excerpts from "Diseases of the Nose and Throat," 1948,

Thomson, Excerpts from "Diseases of the Nose and Throat," 1955.

Kurlander et al., "Therapeutic Valve of the Pneumatic Dilator in Achalasia of the Esophagus."

Van Goidsenhoven, "Treatment of Achalasia of the Cardia with Pneumatic Dilations."

Weinbeck, "Die Pneumatische Dilation zur Behandlung der Achalasie der Speiserohre."

Kugimiya, "The Use of Fogarty Balloon Catheter for Dilatation of Postoperative Esophageal Stricture," Kyogu Geka, vol. 30/5.

Friedberg, "Dilatation of Esophageal Strictures in Childresm Using a Fogarty Balloon Catheter," *The Journal of Otolaryngology*, 8:6, 1979, p. 541.

Earlam et al., "Benign Oesophageal Strictures: Historical and Technical Aspects of Dilatation," *The British Journal of Surgery*, vol. 68:12 (1981).

London et al., "Dilatation of Severe Esophageal Strictures by an Inflatable Balloon Catheter," Gastroenterology, 1981:80:173–75.

Kollath et al., "Dilatation of Esophageal Stenosis by Balloon Catheter, Cardiovascular and Interventional Radiology," (184) 7:35–39.

de Feyter, "Short Term Results of Percutaneous Transluminal Coronary Angioplasty with the Monorail Technique Experience in the First 1000 Patients," British Heart Journal 1990, 63:235–239.

Ellis et al., "Excerpts from Achalasia of the Esophagus," pp. 122–147, vol. IX in the series Major Problems in Clinical Surgery, J. Dunphy, M.D., Ed. (1969).

Nordenstrom, "Ballon Catheters for Percutaneous Insertion into the Vascular System", ACTA Radiology, vol. 57, pp. 411–416 (1962).

Nordenstrom, "New Instruments for Catherization and Angiocardiography, Radiology," vol. 85, pp. 256–259 (1965).

Nordenstrom, "Percutaneous Balloon Occlusion of the Aorta," ACTA Radiology, vol. 4, p. 365 (1966).

Olsen, "The Treatment of Cardiospasm: Analysis of a Twelve–Year Experience," (1951).

Siegel et al., "A New Dimension of Therapeutic Endoscopy," Endoscopy, vol. 16, pp. 231–236 (1984).

Vantrappen et al., "Treatment of Achalasia with Pneumatic Dilations," Gut., vol. 12, pp. 268–275 (1971).

* cited by examiner

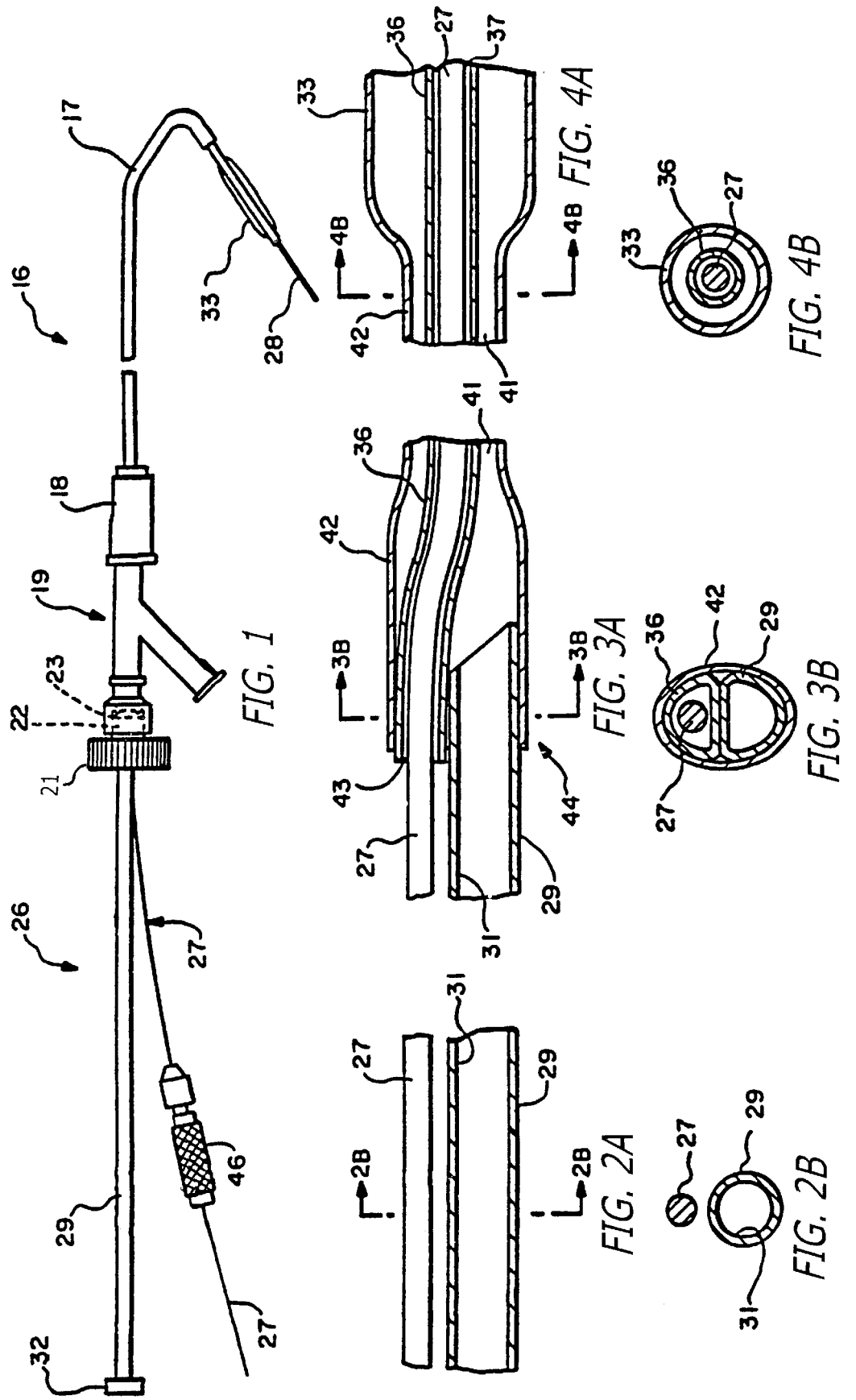

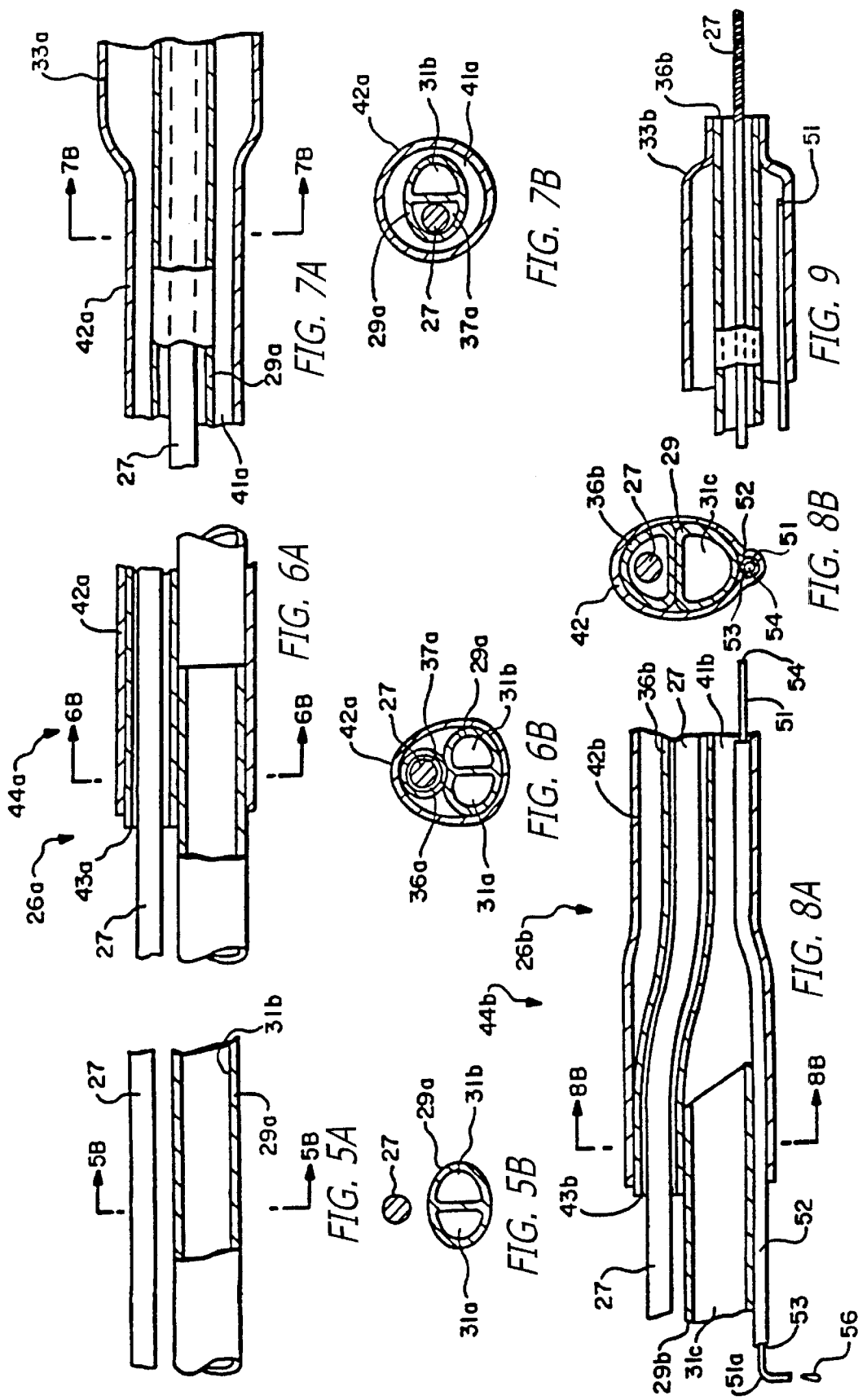

ANGIOPLASTY APPARATUS FACILITATING RAPID EXCHANGES

This is a continuation application of application Ser. No. 08/208,972 which was filed on Mar. 9, 1994, now U.S. Pat. No. 5,451,233 which is a divisional of Ser. No. 08/010,458, filed Jan. 27, 1993, now U.S. Pat. No. 5,300,085, which is a continuation of Ser. No. 07/937,977, now Pat. No. 5,350,395, filed Nov. 2, 1992, which is a continuation of Ser. No. 07/774,479, filed Oct. 10, 1991, now abandoned which is a continuation of Ser. No. 07/548,200, filed Jul. 5, 1990, now U.S. Pat. No. 5,061,273, which is a continuation of Ser. No. 07/361,676, filed Jun. 1, 1989 now abandoned which is a continuation of Ser. No. 07/117,357, filed Oct. 27, 1987 now abandoned, which is a continuation of Ser. No. 06/852,197, filed Apr. 15, 1986 now abandoned.

This invention relates to angioplasty apparatus facilitating rapid exchanges and a method for making rapid exchanges of angioplasty devices.

At the present time in practicing angioplasty, it is often necessary to exchange one dilatation catheter for another. In doing so, it has been necessary to utilize long exchange wires having a length of approximately 300 centimeters which typically requires two operators to perform the procedure. During this procedure, it is necessary that the operators communicate with each other which makes the procedure time consuming. In addition, since the exchange wire is so long it often is awkward to handle and for that reason may come in contact with the floor or become contaminated which necessitates removing the entire apparatus being utilized for the angioplasty procedure. There is therefore a need for a new and improved angioplasty apparatus which overcomes such difficulties.

In general, it is an object of the present invention to provide an angioplasty apparatus and a method which facilitates rapid exchanges of various types of devices.

Another object of the invention is to provide an angioplasty apparatus and method of the above character which greatly facilitates exchanges of dilatation catheters.

Another object of the invention is to provide an angioplasty apparatus and method of the above character which can be utilized for the positioning of flexible elongate members.

Another object of the invention is to provide an angioplasty apparatus and method of the above character which can be utilized with various types of devices utilizing flexible elongate members.

Another object of the invention is to provide an angioplasty apparatus and method in which dye injection and pressure measurements can. be made.

Additional objects and features of the invention will appear from the following description in which the preferred embodiments are set forth in conjunction with the accompanying drawings.

FIG. 1 is a side elevational view of an angioplasty apparatus incorporating the present invention.

FIGS. 2A, 3A and 4A are partial cross sectional views of the shaft, transition and balloon regions of the balloon dilatation catheter utilized in the embodiment of the invention shown in FIG. 1.

FIGS. 2B, 3B and 4B are cross sectional views taken along the lines 2B—2B, 3B—3B and 4B—4B of FIGS. 2A, 3A and 4A respectively.

FIGS 5A, 6A and 7A are cross sectional views corresponding to FIGS. 2A, 3A and 4A of another embodiment of a balloon dilatation catheter incorporating the present invention.

FIGS. 5B, 6B and 7B are cross sectional views taken along the lines 5B—5B, 6B—6B and 7B—7B of FIGS. 5A, 6A and 7A respectively.

FIGS. 8A and 9 are cross sectional views of the transition and balloon regions of another balloon dilatation catheter incorporating the present invention.

FIG. 8B is a cross sectional view taken along the line 8B—8B of FIG. 8A.

Figure 10:
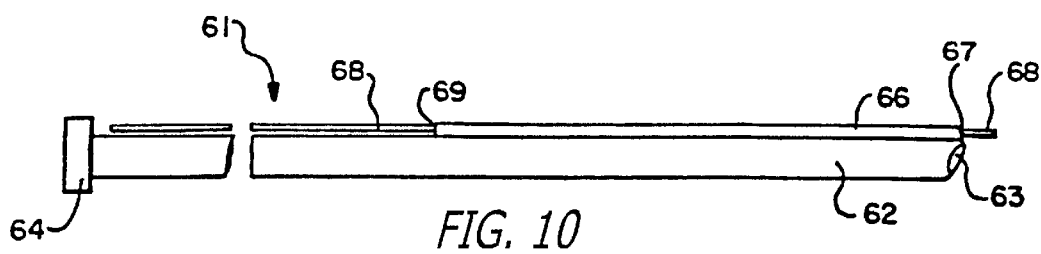
FIG. 10 is a side elevational view of a dedicated dye injection/pressure measurement catheter incorporating the present invention.

In general, the angioplasty apparatus of the present invention is designed for introduction into the vessel of a patient. It consists of a guiding catheter which is adapted to be inserted into the vessel of the patient. It also consists of a device which is adapted to be inserted into the guiding catheter. The device includes a flexible elongate member, a sleeve. is secured to the flexible elongate member near the distal extremity thereof and extends from the distal extremity into a region spaced from the distal extremity of the flexible elongate member. The device also includes a guide wire which is adapted to extend through the sleeve from the distal extremity of the flexible elongate element, through the sleeve and rearwardly of the sleeve alongside of and exteriorally of the flexible elongate element.

More particularly as shown in FIGS. 1–4, the angioplasty apparatus 16 for facilitating rapid exchanges of dilatation catheters consists of a conventional guiding catheter 17 which is provided with a rotatable hemostatic adapter 18 mounted on a proximal end and a y or two-arm connector or adapter 19 which is mounted on the rotatable adapter 18. The y-connector 19 is provided with a knurled knob 21 which carries a threaded valve member 22 that carries an O-ring 23 which is adapted to be urged into sealing engagement with a balloon dilatation catheter 26 and a guide wire 27 extending through the y-adapter 19 and through the guiding catheter 17 as shown in. FIG. 1.

The balloon dilatation catheter 26 is of a single lumen type and is provided with a flexible elongate tubular member 29 which has a lumen 31 extending therethrough. The flexible tubular member 29 can be formed of a suitable material such as plastic. A Luer-type fitting 32 is mounted on the proximal extremity of the flexible tubular member 29 and is adapted to be connected to a syringe or other type of instrument for introducing a radiographic contrast liquid into the flexible tubular member 29. A balloon 33 is mounted on the distal extremity of another flexible tubular member 36 also is formed of a suitable material such as plastic. The distal. extremity of the balloon 33 is bonded to the distal extremity of the flexible tubular member 36 to form an air-tight and liquid-tight seal with respect to the same. The balloon 33 is coaxial with the tubular member 36 or sleeve as shown in FIG. 4B. The flexible tubular member 36 is provided with a guide wire lumen 37 through which the guide wire 27 carrying its flexible tip 28 can extend.

Means is provided for forming a balloon inflation lumen 41 substantially concentric with the flexible tubular member 36 and extends toward the distal extremity of the flexible tubular member 36. As can be seen from FIGS. 3B and 4B, the balloon inflation lumen 41 is formed by a flexible tubular member 42 which can be formed integral with the balloon 33. The flexible tubular member 42 extends into. a transition region 44 which overlies the distal extremity of the flexible tubular member 29 so that the lumen 31 therein is in communication with the balloon inflation lumen 41. As can be seen particularly from FIG. 3A, the flexible tubular member 36 makes a transition and extends out of the tubular member 42 and provides an opening 43. The proximal extremity of the tubular member 36 overlies the flexible tubular member 31. The guide wire 27 exits through the opening 43 and extends alongside and exteriorly of the flexible tubular member 29 from the proximal extremity of the flexible tubular member 36 to the proximal extremity of the flexible tubular member 29.

The transition region 44 should be positioned at least approximately 10–15 centimeters from the distal extremity of the balloon dilatation catheter 26. This is important for two reasons. One is that the transition region be kept at a point where when the balloon dilatation catheter 26 is utilized in a procedure, the transition region remains in the guiding catheter 17 and out of the coronary artery. The spacing from the distal extremity of the dilatation catheter for the transition region is also advantageous in that it permits the person performing the procedure to pull the balloon dilatation catheter 26 out of the guiding catheter 17 until the transition region 44 clears the y-connector 19 so that all-of the portion of the guide wire 27 which is exterior of the balloon dilatation catheter 26 is proximal of the y-connector. While this is being done, the operator can then utilize the knurled nut 21 to again close the o-ring to form a hemostatic seal between the y-connector-and the balloon dilatation catheter to minimize the loss of blood from the patient.

The flexible tubular member 42 can be formed of a suitable material such as a heat shrinkable plastic so that it can be shrunk onto the distal extremity of the flexible tubular member 29 and onto the proximal extremity of the flexible tubular member 36 to form liquid-tight and air-tight seals with respect to the same. From the construction shown it can be seen that the guide wire 27 exits from the balloon dilatation catheter 26 in a region which is relatively close to the distal extremity of the balloon dilatation catheter 26 and extends exteriorly of the balloon dilatation catheter to the proximal extremity of the same. As shown in FIG. 1, the guide wire 27 and the balloon dilatation catheter 26 prextend outwardly from the y-connector 19.

A torquer 46 of a conventional construction is secured to the guide wire 27 for rotating the guide wire as hereinafter described.

Operation and use of the angioplasty apparatus shown in FIG. 1 may now be briefly described as follows. The guiding catheter 17 is inserted into the coronary artery in a conventional manner. The balloon dilatation catheter is prepared for insertion into the guiding catheter 17 in a conventional manner. The balloon 33 can be inflated outside the body by the use of a balloon flushing tube of the type described in U.S. Pat. No. 4,323,071 and inflated by introducing a radiopaque liquid through the fitting 32 into the lumen 31 and through the lumen 41 into the balloon 33 to flush all of the air in the balloon 33 through the balloon flushing tube to fully inflate the balloon. After the balloon 33 has been inflated, the balloon can be deflated by removing the radiopaque liquid from the balloon.

The guide wire 27 is then introduced into the balloon dilatation catheter 26 by a back loading technique. without the torquer 46 on the guide wire, the proximal extremity of the guide wire 27 is inserted backwardly through the tip of the balloon dilatation catheter through the guide wire lumen 37. The guide wire is advanced rearwardly by holding the distal extremity of the balloon dilatation catheter in one hand and advancing the guide wire 27 rearwardly with the other hand until the guide wire 27 exits through the opening 43 at the transition region 44 of the dilatation catheter. As soon as the guide wire has cleared the opening 43, the guide wire can be grasped by the hand and pulled rearwardly paralleling the balloon dilatation catheter 26 until its proximal extremity is near the proximal extremity of the dilatation catheter and so that the distal extremity of the guide wire 27 with its flexible or floppy tip 28 protrudes at least partially from the distal extremity of the balloon dilatation catheter.

At this point in time, the O-ring 23 in the y-connector 19 is opened by operation of the knurled knob 21. The distal extremity of the balloon dilatation catheter 26 having the flexible tip protruding therefrom is then introduced to the y-connector past the opened o-ring 23 and slid down the guiding catheter 17. The balloon dilatation catheter 26 and the guide wire 27 are grasped between the fingers of a hand and are advanced parallel into the guiding catheter 17. This procedure is continued until a substantial portion of the balloon dilatation catheter is disposed in the guiding catheter 17.

The torquer 46 now can be attached to the guide wire 27 near the proximal extremity of the same. The guide wire 27 is then advanced ahead of the balloon dilatation catheter until it enters the arterial vessel of the patient. The balloon dilatation catheter 26 is held stable by the fingers of the hand while the guide wire 27 is being advanced. The positioning of the guide wire. 27 in the desired arterial vessel can be observed under a fluoroscope by using x-ray techniques well known to those skilled in the art. As is well known to those skilled in the art, the torquer 46 can be utilized for rotating the guide wire 27 to facilitate positioning of the flexible tip 28 in the desired arterial vessel so that the distal extremity of the guide wire can be advanced into the stenosis which it is desired to open or enlarge.

As soon as the guide wire 27 is in the desired location, it can be held stationary by two fingers of the hand and at this point in time, the balloon dilatation catheter 26 is advanced over the guide wire until the deflated balloon 33 is across the desired lesion or stenosis. If any difficulty is encountered by the person conducting the procedure in introducing the balloon dilatation catheter so that the balloon 33 resists crossing the lesion or stenosis, the guide wire 27 can be retracted slightly. The person then can observe under the fluoroscope to see that the tip 218 of the guide wire is wiggling in the blood stream indicating that it is free to move in the blood stream. Then the person can grasp both the guide wire and the dilatation catheter in one hand and advance them as a unit so that they can cross the stenosis as a unit. It has been found by utilizing such a procedure, greater pushability can be obtained in advancing the balloon dilatation catheter across the stenosis. In other words, more force can be applied to the balloon to cause it to cross the stenosis or lesion in case the opening therein is very small.

After the balloon 33 has crossed the stenosis or lesion, the balloon 33 can be inflated in a conventional manner by introducing a radiopacue contrast liquid through the lumen 31. After the inflation has occurred and the desired operation has been performed by enlarging the opening in the stenosis, the balloon dilatation catheter 26 can be removed very rapidly by the person performing the procedure by grasping the guide wire 27 by two fingers immediately proximal of the y-connector 19 after the torquer 46 has been removed. The balloon dilatation catheter 26 can be removed in several seconds in comparison with the much longer time required for removing the balloon dilatation catheter utilizing prior art exchange wire procedures. As soon as the balloon dilatation catheter 26 has been removed from the guiding catheter 17, another injection of radiographic contrast liquid can be introduced through the guiding catheter 17 to observe whether or not the balloon dilatation procedure which has been performed on the lesion or stenosis has in fact opened the lesion or stenosis to the satisfaction of the person performing the procedure.

If it is ascertained by the person performing the procedure that additional dilation of the stenosis is desired and that a larger balloon should be inserted into the stenosis, this can be accomplished very rapidly by selecting the desired size of balloon dilatation catheter.

As the balloon dilatation catheter 26 is being retracted out of the guiding catheter 17 and as soon as the transition region 44 has cleared the y-adapter 19, the o-ring 23 can be tightened down to form a seal over the balloon dilatation catheter to minimize the loss of blood of the patient. Thereafter, if desired, the remainder of the balloon dilatation catheter 26 can be removed from the guiding catheter 17 until the proximal extremity of the guide wire passes through the opening 43 and passes through the end of the balloon dilatation catheter 26. As soon as this has been accomplished, a new balloon dilatation catheter can be loaded onto the guide wire in a rearward direction by introducing the proximal extremity of the guide wire 27 into the tip of the balloon dilatation catheter. As this is being done, the index finger of the hand performing the procedure can be utilized for opening the o-ring by adjusting the knurled knob 21. The guide wire 27 is grasped by the fingers of the hand and the balloon dilatation catheter 26 can be advanced rapidly over the guide wire into the guiding catheter 17 and advanced across the lesion in a manner hereinbefore described with respect to the smaller balloon dilatation catheter which had been utilized. The balloon of the new dilatation catheter can be inflated in the same manner as hereinbefore described. If necessary even another exchange procedure can be readily accomplished in the same manner as hereinbefore described utilizing a still larger balloon dilatation catheter if that turns out to be necessary.

It has been found that an exchange utilizing the present angioplasty apparatus can be performed in less than 10 to 15 seconds whereas in the past utilizing a prior art guide wire exchange procedure required an average of approximately two minutes.

After the desired amount of dilation of the stenosis or lesion has been accomplished, the balloon dilatation catheter 26 can be removed and thereafter, the guiding catheter 17 can be removed. Another emodiment of an angioplasty apparatus incorporating the present invention is shown in FIGS. 5A and 5B, 6A and 6B and 7A and 7B in which an additional dye/pressure lumen has been incorporated into the apparatus in order to enable an injection of a distal dye through the balloon dilatation catheter and also to enable the measurement of pressures at the tip of the balloon dilatation catheter. The construction which is utilized is very similar to that shown in the balloon dilatation catheter 26 shown in FIG. 1. The corresponding parts of the balloon dilatation catheter 26a shown in FIGS. 5–7 is very similar to that hereinbefore described and for that reason the corresponding parts have been given the same corresponding numbers with letters being added to the numerals where changes are present in the parts or components. Thus the tubular member 29a, rather than having a single lumen 31 is provided with dual lumens 31a and 31b disposed:* side by side in the shaft region of the balloon dilatation catheter as shown in FIGS 5A and 5B. In the transition region 44a, the two lumens 31a and 31b are still disposed side by side with the lumen 37a for the guide wire being disposed above the lumens 31a and 31b. In the balloon region, the lumen 31a has been terminated and extends into the balloon lumen 41a. At the transition region 44a, the guide wire lumen 37a inclines downwardly and sidewise and adjoins the lumen 31b through the distal extremity of the balloon dilatation catheter 26a. The lumen 31b extends to the distal extremity of the balloon dilatation catheter.

The balloon dilatation catheter which is shown in FIGS. 5–7 can be utilized in the same manner as the balloon dilatation catheter shown in FIG. 1. It can be seen that the guide wire 27 extends out of the opening 43a in the transition region 44c and parallels the balloon catheter to its proximal extremity. A balloon dilatation catheter of the type shown in FIGS. 5–7 can be utilized initially in an angioplasty procedure. However, it should be appreciated that if a very small opening is present in the stenosis or lesion, it may be desirable to utilize a balloon dilatation catheter of the type shown in FIG. 1 first because it can be constructed with a smaller diameter than a balloon dilatation catheter of the type shown in FIGS. 5–7 because of the additional lumen which is provided for dye injection and pressure measurements. After a smaller balloon dilatation catheter has been utilized, a balloon dilatation catheter of the type is shown in FIGS. 5–7 can be used utilizing the exchange procedure hereinbefore described to make dye injection and/or pressure measurements through the use of the additional lumen 31b. It is particularly desirable to make such a pressure measurement before conclusion of the angioplasty procedure to be sure that the proper dilation of the lesion or stenosis has occurred and that there is adequate blood flow through the lesion or stenosis.

Still another embodiment of the angioplasty apparatus incorporating the present invention is shown in FIGS 8A and 8B and shows the transition region of a balloon dilatation catheter 26b which incorporates a vent tube 51 which is utilized for venting air from the balloon. during inflation of the balloon and before insertion into the patient with radiopaque liquid to ensure that all the aid is exhausted from the balloon. As shown in the transition region 44b in FIG. 8A, the guide wire 27 extends through an opening 43b provided in the transition region and extends through a flexible tubular member 36b out the end of the balloon dilatation catheter as shown in FIG. 9. A balloon filling lumen 31c is provided by the flexible tubular member 29b and terminates in the transition region 44b where it opens into the balloon filling lumen 41b that opens into the interior of the balloon 33b. A relatively short sleeve 52 formed of a suitable material such as plastic is also provided in the transition region 44b and as shown in FIG. 8A underlies the flexible tubular member 29b and extends from a region forward of the flexible tubular member 42b and terminates distally within the balloon inflation lumen 41 as shown in FIG. 8A.

The sleeve 52 is provided with a lumen 53 through which the vent tube 51 extends. The vent tube 51 can be formed of a suitable material such as metal and is also provided with a lumen 54 of a size so that gas can escape therethrough. The proximal extremity of the vent tube 51 is provided with a portion 51a which is bent at right angles to the main portion of the vent tube 51 to ensure that the vent tube will be removed from the balloon dilatation catheter 26b prior to insertion into the guiding catheter 17. As shown in FIG. 9, the vent tube 51 extends into the balloon 33 into a region near the distal extremity of the same.

Operation of the balloon dilatation catheter 26b shown in FIGS. 8A, 8B and 9 may now be briefly described as follows. With the vent tube 51 in place in the balloon dilatation catheter, radiopaque contrast liquid is introduced through the balloon inflation lumen 31 and through the balloon inflation lumen 41b to introduce the liquid into the balloon. As the liquid is introduced into the balloon, any air in the balloon is discharged through the vent tube 51. Pressure is maintained on the radiopaque contrast liquid introduced into the balloon until droplets 56 of the liquid exit from the proximal extremity of the vent tube 51 which serves to indicate that the balloon has been completely filled with the radiopaque contrast liquid and that all of the air therein has been exhausted therefrom. As soon as this occurs, the vent tube 51 can be withdrawn completely from the balloon dilatation catheter. The sleeve 52 which carries the vent tube collapses upon withdrawal of the vent tube and will remain collapsed to provide a valve to prevent the, escape of any additional radiopaque contrast liquid from the balloon 33b. The sleeve 52 remains collapsed because when a high pressure is being introduced through the balloon inflation lumen 31c, the flexible tubular member 29b will force collapsing of the sleeve 52. Alternatively, when a negative pressure is being applied to the balloon 33b as, for example, when the balloon is being deflated, the positive atmospheric pressure on the exterior of the flexible tubular member 42b will again cause collapsing of the sleeve 52. Thus in effect there is provided a double valve system in which positive pressures on the interior will collapse the sleeve and when there is negative internal pressure the positive exterior atmospheric pressure will collapse the sleeve.

In all other respects, the balloon dilatation catheter 26b: can be utilized in the same manner as the balloon dilatation catheters hereinbefore described in connection with exchanges on the guide wire 27.

Still another embodiment of an angioplasty apparatus incorporating the present invention is shown in FIG. 10 in which there is disclosed a dedicated pressure/dye catheter 61. The pressure/dye catheter 61 consists of an elongate flexible tubular member 62 formed of a suitable material such as plastic which is provided with a pressure dye lumen 63 extending therethrough. The proximal extremity of the tubular member 62 is provided with a Luer-type fitting 64 to which devices having Luer-type fittings can be attached. A sleeve 66 formed of a suitable material such as plastic is secured to the exterior of the flexible tubular member 62 by suitable means such as an adhesive. It is provided with a guide wire lumen 67 extending therethrough. It should be appreciated that the sleeve 66 can be formed integral with the flexible tubular member 62 if desired. The sleeve 66 extends for a distance of at least 10 to 15 centimeters from the distal extremity of the catheter 61 so that the transition region where it terminates at its proximal extremity is be within the guiding catheter 17 so that the transition region does not enter into the arterial vessel of the patient. A guide wire 68 is provided which extends through the guide wire lumen 67. The guide wire 68 can be of the same type as the guide wire 27. It is inserted into the sleeve 66 by taking the proximal extremity of the guide wire which is relatively stiff and inserting it into the distal extremity of the sleeve-and then pushing it backwardly or rearwardly through the sleeve until it clears the opening 69: at the proximal extremity of the sleeve 66. The guide wire 68 is then pulled so that it extends in a direction parallel to the flexible tubular member 62 into a region near the proximal extremity of the tubular member 62.

It can be readily seen from the foregoing description that the pressure/dye catheter 61 can be readily introduced into a guiding catheter 17 and that the distal extremity of the pressure/dye catheter can be positioned in a desired location in the arterial vessel by utilizing the guide wire 68 to position the same. It also should be appreciated that a torquer of the type hereinbefore described such as the torquer 46 can be utilized. on the proximal extremity of the guide wire 68 to cause rotational movement of the guide wire to facilitate positioning of the guide wire in the desired arterial vessel and to thereafter have the tubular member 62 follow the same. The desired picture and/or dye measurements can then be made by utilizing the lumen 63 provided in the tubular member 62. As can be seen from FIG. 10 the distal extremity of the tubular member 62 can be slanted and rounded as shown to facilitate entry into the stenosis in the arterial vessel. This is desirable because of the eccentricity created by the addition of the sleeve 66.

Figure 11:
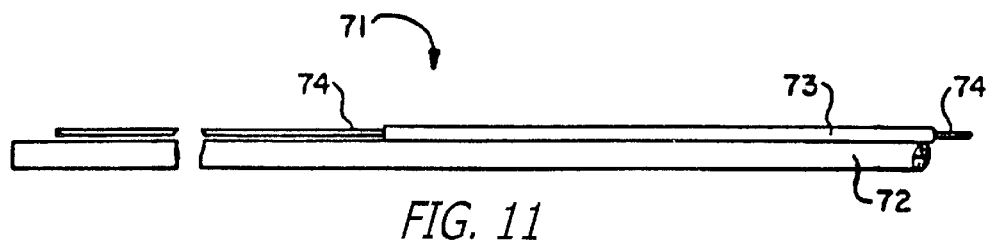
FIG. 11 is a side elevational view of a fiber optic cable incorporating the present invention.

Another embodiment of an angioplasty apparatus is shown in FIG. 11 and takes the form of a fiber optic device 71. An encased fiber optic bundle 72 which is generally circular in cross section is provided. A sleeve 73 of the type hereinbefore described formed of a suitable material such as plastic is secured to the distal extremity of the fiber optic bundle 72 which is adapted to receive a guide wire 74. As in the previous embodiments, the sleeve 73 extends from the distal extremity for a distance of approximately 10 to 15 centimeters after which the guide wire exits from the sleeve and extends alongside and exteriorally of the fiber optic bundle 72 for substantially the entire length of the fiber optic bundle. As with the previous devices, the guide wire 74 is threaded into the sleeve by taking the proximal extremity or stiff end of the guide wire and inserting it at the distal extremity of the sleeve 73 and pushing it from the rear towards the forward extremity of the sleeve. The fiber optic device 71 can then be inserted into a guiding catheter 17 and advanced to the desired location through the use of the guide wire. The fiber optic bundle then can be utilized for angioscopy for looking directly at the blood vessel or alternatively, for delivering energy to plaque in the blood vessel to perform laser angioplasty. It should be appreciated that steerable systems can be utilized for directing the distal extremity of the fiber optic bundle if that is desired. It should be appreciated that the concept of using a relatively short sleeve extending from the distal extremity of the device to a region approximately 10 to 15 centimeters to the rear and then having the guide wire extend externally of the device is applicable for a number of medical devices as well as other applications. For example, ultrasonic catheters for imaging ultrasound and for measurement of Doppler velocity can be utilized to provide various types of dedicated devices having the guide sleeve with the guide wire therein for facilitating positioning of the same in arterial vessels. The apparatus of the present invention is particularly useful in devices where multiple re-entries are required in order to complete the procedure.

Figure 12:
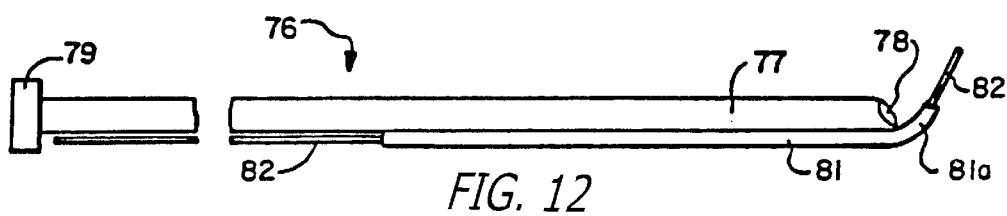
FIG. 12 is a side elevational view of a dedicated dye injection/pressure measurement catheter incorporating the present invention and having specific guiding means. for facilitating. entering acute bends in arterial vessels.

In FIG. 12, there is disclosed another embodiment of an angioplasty apparatus to provide a pressure dye catheter 76 having additional steering capabilities. It consists of a flexible tubular member 77 formed of a suitable material such as plastic which is provided with a lumen 78 extending through a slanted and curved end. A Luer-type fitting 79 is-provided on the proximal extremity. A sleeve 81 formed of a suitable material such as plastic is secured to the distal extremity of the flexible elongate member. 77. The sleeve is provided with a curved portion: 81a which extends slightly beyond the distal extremity of the flexible elongate member 77 and curves over the end of the flexible elongate member 77. The guide wire 82 extends through the sleeve 81 as shown. The catheter shown in FIG. 12 can be utilized in situations where there is an acute bend. in the arterial vessel. By using the catheter shown in FIG. 11, the guide wire can be directed into the acute bend by rotation of the catheter 76 to help direct the guide wire into the acute bend. After the acute bend has been negotiated by the guide wire, the distal extremity of the catheter can follow the guide wire and negotiate the acute bend. The desired pressure and/or dye measurements can then be made. If by chance a guide wire should enter the wrong vessel, the guide wire can be retracted into the sleeve and then the catheter itself can be reoriented to have the distal extremity of the sleeve 81 directed. into the proper region so that the guide wire will enter the proper arterial vessel. The catheter 76 shown in FIG. 12 can be introduced into the guiding catheter 17 in the same manner as the other catheters hereinbefore described.

Figure 13:
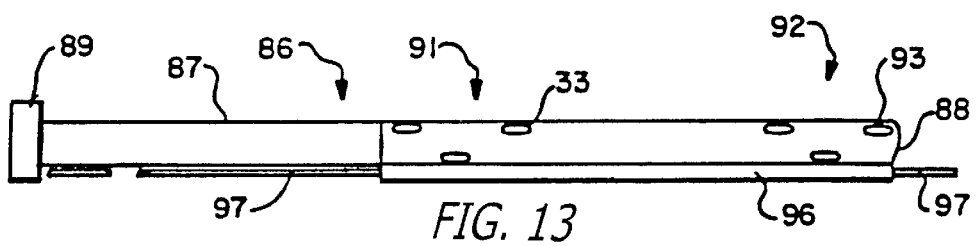
FIG. 13 is a side elevational view of a bail out catheter incorporating the present invention.

Still another embodiment of the angioplasty apparatus of the present invention is shown in FIG. 13 in the form of a bailout catheter 86. The bailout catheter 86 consists of a flexible tubular member 87 formed of a suitable material such as plastic which is provided with a lumen 88 extending therethrough. A Luer-type fitting 89 is secured to the proximal extremity of the tubular member 87. The distal portion of the tubular member 87 is provided with two sets 91 and 92 of holes 93 which are spaced circumferentially and apart longitudinally of the tubular member. A sleeve 96 formed of a suitable material such as plastic is secured to the distal extremity of the tubular member 87 and extends from the distal extremity of the tubular member 87 into a region 10 to 15 centimeters from the distal extremity and is adapted to receive a guide wire 97 which extends through the same. The guide wire 97 is inserted into the sleeve by taking the proximal extremity of the guide wire and inserting it into the distal extremity of the sleeve and pushing it rearwardly into the sleeve until it exits from the sleeve. The guide wire 97 is then pulled in a direction generally parallel to the flexible tubular member 87 until it is adjacent the fitting 89.

The bailout catheter 86 is utilized in situations where an obstruction has occurred in a blood vessel and stops the flow of blood. In order to reestablish the flow of blood, the bailout device is inserted into the guiding catheter 17. If a guide wire is already in place, the bailout device can be placed on the guide wire by introducing the proximal extremity of the guide wire into the sleeve and then pushing the bailout catheter on the guide wire into the guiding catheter 17 until it passes through the obstruction in the arterial vessel. The distal extremity of the bailout device is so positioned so that the obstruction is disposed between the two sets of holes 91 and 92. When the bailout catheter is positioned, blood can still flow through the holes 93 past the obstruction which is held out of the way by the bailout catheter.

Thus it can be seen that the same principle utilizing a guide tube and an external guide wire passing through the guide tube can be utilized for positioning the bailout device. As pointed out previously, the bailout device can be utilized for positioning other types of devices in arterial vessel, as for example, atherectomy devices particularly where multiple re-entries or reintroductions of the devices are required.

Figure 14:
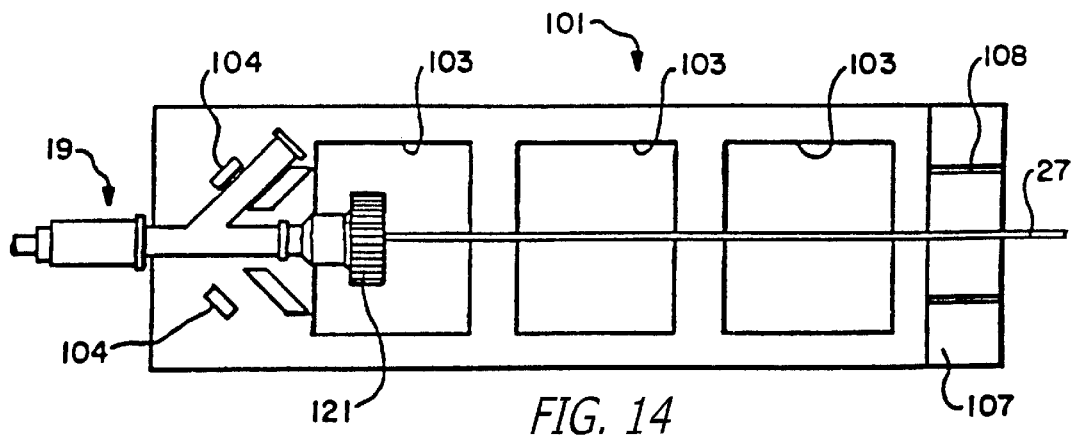
FIG. 14 is a plan view of a holder utilized in connection with the present invention.

In FIG. 14 there is disclosed additional angioplasty apparatus in which a holder 101 is provided which serves as a support structure for a y-type connector 19 of the type hereinbefore described in conjunction with the angioplasty apparatus shown in FIG. 1. The holder 101 consists of a rectangular member 102 which is generally planar. The member 102 can be formed of a suitable material such as plastic and is provided with a plurality of rectangular openings 103 extending longitudinally of the same to lighten the same. Posts 104 are provided on the forward extremity of the member 102 and are adapted to receive the y-type connector 19 and to hold it in place on the member 102. When positioned in the posts 104, the knurled knob 21 extends into one of the openings 103 so that it can be readily operated. A block 107 is carried by the other end of the member 102 and, if desired, can be formed intergal therewith. The block is provided with a plurality of spaced apart slots 108 which are adapted to frictionally engage and receive the guide wire 27. The friction block 107 should be positioned a suitable distance as, for example, 15 to 20 centimeters from the o-ring carried by the y-connector 19.

Use of the holder 101 shown in FIG. 14 may now be briefly described as follows. The holder 101 can be placed on the operating table near the region where the guiding catheter 17 has been inserted into the patient, as for example, in a femoral artery in the leg of a patient. After the guide wire has been inserted into the guiding catheter, the proximal end or, in other words, the stiff end of the guide wire can be placed in the friction clamp 108. When it is desired to utilize a dilatation catheter, the end of the guide wire which has been positioned in the clamp can be lifted out of the slot 108 and inserted into the sleeve carried by the distal extremity of the dilatation catheter by taking the proximal end and advancing it from the tip rearwardly through the sleeve. As soon as the guide wire has been introduced through the sleeve, the proximal extremity of the guide wire can be-repositioned in the slot 108. Thereafter, the dilatation catheter can be advanced independently without the operator needing to pay any attention to the guide wire which is held in the desired position by the holder 101. Similarly, the holder can be utilized to keep the guide wire in place while the dilatation cathether is being briskly withdrawn.

More than one of the slots 108 has been provided in the holder 101 in order to make it possible to accommodate two wire or two balloon dilatation catheters in which one of the other slots 108 can be utilized for accommodating the additional guide wire. This prevents the guide wires from becoming entangled with each other.

It is apparent from the foregoing that there has been provided an angioplasty apparatus which greatly facilitates the exchange of devices which utilize flexible elongate elements as a part thereof. Rapid exchanges are possible with only one person being necessary to make the exchanges. The need for long exchange wires has been eliminated. One device can be readily substituted for another utilizing the same guide wire which has already been positioned. It can be seen from the foregoing that a relatively simple and expedient solution has been provided which eliminates the need for long exchange wires and the danger of those exchange wires becoming contaminated.

Although the present invention has been described principally in conjunction with catheters having coaxial lumens, it should be appreciated that the invention is as applicable, if not more applicable, to catheters having side-by-side lumens.

What is claimed is:

1. An intravascular assembly for performing a therapeutic or diagnostic procedure within a human patient's body and which is configured for percutaneous introduction into and advancement within the patient's vasculature to the location where the procedure is to be performed, comprising:

a) an intravascular catheter having
   an elongated catheter shaft which has proximal and distal ends, a distal shaft section which is configured for advancement through the patient's vasculature to a location within the patient's body where the procedure is to be performed, a proximal shaft section which is much longer than the distal shaft section and which is configured to have a distal portion within the patient and a proximal portion thereof extending out of the patient during the procedure, a distal guidewire opening in the distal end of the shaft, a proximal guidewire opening spaced at least about 10 cm proximally from the distal end of the catheter shaft and a relatively long distance distally from the proximal end of the catheter shaft so as to remain within the patient during the procedure, a therapeutic or diagnostic member on the distal shaft section to perform the procedure which is configured for percutaneous introduction into and advancement through the patient's vasculature to the location where the procedure is to be performed and which is spaced closer to the distal end of the catheter shaft than to the proximal guidewire opening, a guidewire passageway which extends between and is in fluid communication with the distal guidewire opening and the proximal guidewire opening; and b) a guidewire which has an elongated shaft and a flexible distal extremity, which is configured for advancement within the patient's vasculature, which is longer than the intravascular catheter and which is slidably disposed within the guidewire passageway of the intravascular catheter to facilitate delivery of the catheter thereover to the location within the patient's body where the procedure is to be performed.

2. In an intravascular assembly for performing a therapeutic or diagnostic procedure within a region of a human patient's body which is configured for percutaneous introduction into the patient's vasculature and for intravascular delivery to a region within the patient's body where the procedure is to be performed, the combination comprising:

a) an elongated catheter which has an elongated catheter shaft with proximal and distal ends, a distal shaft section which is configured to be introduced into and advanced within the patient's vasculature and a proximal shaft section which is much longer than the distal shaft section and which is configured to have a distal portion within the patient and a proximal portion thereof extending out of the patient during the procedure, a distal guidewire port in the distal end of the shaft, a proximal guidewire port spaced a relatively short distance of at least 10 cm proximally from the distal end of the shaft and a relatively long distance distally from the proximal end of the shaft so as to be disposed within the patient when the procedure is performed, a means to perform the procedure on the distal shaft section which is configured for percutaneous introduction and advancement within the patient's vasculature and which is spaced closer to the distal end of the shaft than to the proximal guidewire port, and a guidewire passageway which extends between the distal guidewire port and the proximal guidewire port; and b) an elongated guidewire which has an elongated shaft and a flexible distal extremity, which is longer than the catheter, and which is slidably disposed within the guidewire passageway to facilitate advancement of the catheter over the guidewire through the patient's vasculature to said region while maintaining the position of the guidewire within the patient's vasculature.

3. The intravascular assembly of claim 2 wherein the means to perform the procedure is in communication with an exterior portion of the distal shaft section.

4. In a balloon dilatation catheter assembly for performing an angioplasty procedure within a region of a human patient's coronary artery which is configured for percutaneous introduction into the patient's vasculature and for intravascular delivery to the coronary artery where the procedure is to be performed, the combination comprising:

a) an elongated catheter which has an elongated shaft with proximal and distal ends, a distal shaft section which is configured to be percutaneously introduced into and advanced within the patient's vasculature, a proximal shaft section much longer than the distal shaft section which is configured to have a distal portion within the patient and a proximal portion out of the patient during the procedure and an inflation lumen extending within the proximal and distal shaft sections, a distal guidewire port in the distal end of the shaft, a proximal guidewire port spaced a relatively short distance proximally from the distal end of the shaft and a relatively long distance from the proximal end of the shaft so as to be disposed within the patient's vasculature during the procedure, a dilatation balloon on the distal shaft section which has an interior in fluid communication with the inflation lumen and which is spaced closer to the distal end of the shaft than to the proximal guidewire port, and a guidewire passageway which extends between the distal guidewire port and the proximal guidewire port; and b) an elongated guidewire which is longer than the catheter, and which is disposed within the guidewire passageway to facilitate advancement of the catheter through the patient's vasculature over the guidewire to the patient's coronary artery while maintaining the position of the guidewire within the patient's vasculature.

5. An intravascular catheter for performing a procedure within a region of a human patient's body, comprising:

a) an elongated shaft which is configured for percutaneous introduction into the patient's vasculature, which is long enough for advancement through the patient's vasculature to the region of the patient's body where the procedure is to be performed and which has proximal and distal ends;

b) a distal shaft section which is configured along its length to be percutaneously introduced into and advanced within the patient's vasculature;

c) a proximal shaft section which is much longer than the distal shaft section and which is configured to have a distal portion within the patient and a proximal portion thereof extending out of the patient during the procedure;

d) a distal guidewire opening in the distal end of the shaft;

e) a proximal guidewire opening in the elongated shaft which is spaced at least 10 cm proximally from the distal end of the shaft and a substantially greater distance from the proximal end of the catheter shaft;

f) a therapeutic or diagnostic member on the distal shaft section to perform the procedure which is configured for percutaneous introduction and advancement within the patient's vasculature and which is spaced closer to the distal end of the shaft than the proximal guidewire opening; and g) a guidewire passageway which extends between the distal guidewire opening and the proximal guidewire opening and configured to slidably receive a guidewire therein.

6. A balloon catheter for performing an angioplasty procedure within a human patient's coronary artery, comprising:

a) an elongated catheter shaft with proximal and distal ends, a distal shaft section which is configured to be percutaneously introduced into and advanced within the patient's vasculature, a proximal shaft section which is much longer than the distal shaft section, which is configured to have a distal portion within the patient and a proximal portion thereof extending out of the patient during the procedure and which has an inflation lumen extending within the proximal and distal shaft sections;

b) a distal guidewire opening in the distal end of the shaft;

c) a proximal guidewire opening in the elongated shaft spaced at least about 10 cm proximally from the distal end of the shaft and a substantially greater distance from the proximal end of the shaft;

d) a balloon on the distal shaft section having an interior in fluid communication with the inflation lumen and being spaced closer to the distal end of the shaft than the proximal guidewire port; and e) a guidewire passageway which extends between the distal guidewire opening and the proximal guidewire opening and which is configured to slidably receive a guidewire therein.

7. A balloon dilatation catheter assembly for performing an angioplasty procedure within a region of a human patient's coronary artery comprising a) a guiding catheter having a proximal and a distal end, a shaped distal extremity configured to seat within an ostia of the coronary artery in which the angioplasty procedure is to be performed, a port in the distal end, an inner lumen extending within the guiding catheter to the port in the distal end; and b) an elongated dilatation catheter having
an elongated shaft with proximal and distal ends, a distal shaft section, a proximal shaft section which is much longer than the distal shaft section, which is configured to have a distal portion within the patient and a proximal portion thereof extending out of the patient during the procedure and which has an inflation lumen extending therein,
a distal guidewire port in the distal end of the shaft,
a proximal guidewire port in the distal shaft section spaced a relatively short distance proximally from the distal end of the shaft and a substantially greater distance from the proximal end of the shaft,
a dilatation balloon on the distal shaft section which has an interior in fluid communication with the inflation lumen and which is spaced closer to the distal end of the shaft than to the proximal guidewire port, and
a guidewire passageway which extends between the distal guidewire port and the proximal guidewire port,
the dilatation catheter being slidably disposed within the inner lumen of the guiding catheter and positioned therein so that at least part of the distal shaft section of the dilatation catheter extends out the distal port of the guiding catheter and the proximal guidewire port of the dilatation catheter remains within the inner lumen of the guiding catheter.

8. A balloon catheter which is configured for percutaneous introduction and advancement into a patient's vasculature, comprising:

a) an elongated catheter shaft with
proximal and distal ends,
a distal shaft section which is configured to be percutaneously introduced into and advanced within the patient's vasculature, which includes a first tubular member defining at least in part an inflation lumen and a second tubular member defining at least in part a guidewire passageway,
a proximal shaft section which is much longer than the distal shaft section, which is configured to have a distal portion within the patient and a proximal portion extending out of the patient during the procedure;

b) a distal guidewire opening in the distal end of the shaft which is in fluid communication with the guidewire passageway;

c) a proximal guidewire opening in the elongated shaft which is in fluid communication with the guidewire passageway and which is spaced at least about 10 cm proximally from the distal end of the shaft and a substantially greater distance from the proximal end of the shaft; and d) a balloon on the distal shaft section having an interior in fluid communication with the inflation lumen.

9. The balloon catheter of claim 8 wherein the first tubular member is disposed about the second tubular member.

10. The balloon catheter of claim 9 wherein the first tubular member is at least in part secured to an exterior portion of the second tubular member.

* * * * *

UNITED STATES PATENT AND TRADEMARK OFFICE
CERTIFICATE OF CORRECTION

PATENT NO. : 6,575,993 B1 Page 1 of 1
DATED : June 10, 2003
INVENTOR(S) : Paul G. Yock It is certified that error appears in the above-identified patent and that said Letters Patent is hereby corrected as shown below:

<u>Column 13,</u>
Lines 40, change "ostia" to -- ostium --.

Signed and Sealed this

Third Day of February, 2004

JON W. DUDAS
*Acting Director of the United States Patent and Trademark Office*